United States Patent [19]

Kato et al.

[11] Patent Number: 5,783,442
[45] Date of Patent: *Jul. 21, 1998

[54] CLONING VECTOR PLASMID, VECTOR-PRIMER DERIVED THEREFROM AND PREPARATION METHOD OF CDNA BANK USING THE SAME

[75] Inventors: Seishi Kato, Sagamihara; Takashi Aoki, Tanashi; Yuri Umezawa, Chigasaki, all of Japan

[73] Assignee: Sagami Chemical Research Center, Tokyo, Japan

[*] Notice: The term of this patent shall not extend beyond the expiration date of Pat. No. 5,624,826.

[21] Appl. No.: 709,733

[22] Filed: Sep. 9, 1996

Related U.S. Application Data

[62] Division of Ser. No. 466,111, Jun. 6, 1995, Pat. No. 5,624,826, which is a continuation of Ser. No. 255,799, Jun. 7, 1994, abandoned, which is a continuation of Ser. No. 115,796, Sep. 3, 1993, abandoned, which is a continuation of Ser. No. 606,826, Oct. 31, 1990, abandoned.

[30] Foreign Application Priority Data

Oct. 31, 1989 [JP] Japan ................................ 1-283674
Sep. 7, 1990 [JP] Japan ................................ 2-238332

[51] Int. Cl.⁶ .......................... C12N 15/63; C12N 15/66
[52] U.S. Cl. .................. 435/320.1; 536/23.1; 536/23.4; 536/24.1
[58] Field of Search .................... 435/320.1; 536/23.1, 536/23.4, 24.1

[56] References Cited

U.S. PATENT DOCUMENTS 4,843,003   6/1989   Henikoff et al. ............... 435/91.41
5,238,834   8/1993   Pruitt ............................... 435/172.3
5,624,826   4/1997   Kato et al. ....................... 435/91.4

OTHER PUBLICATIONS

Pharmacia Catalog "Molecular Biologicals" (1986) 67–68.
Mead et al., (1986) Protein Engineering, 1, 67–74.
Deininger (1987) Meth. Enzy. 152, 371–389.
Sargent et al. (1983) Science 222, 135–139.
Okayama et al. (1983) Molec. Cell. Bio. 3, 280–289.
Palazzolo et al., (1987) Gene, vol. 52, pp. 197–206.
Pruitt, Gene, (1988) vol. 66, pp. 121–134.
Helfman et al. (1983) PNAS 80, 31–35.

*Primary Examiner*—Nancy Degen
*Assistant Examiner*—Matthew Latimer
*Attorney, Agent, or Firm*—Birch, Stewart, Kolasch & Birch, LLP

[57] ABSTRACT

A cloning vector plasmid suitable for preparing cDNA banks is disclosed. The cloning vector plasmid of the present invention comprises, in the order mentioned from upstream to downstream unless otherwise specified, a promoter PR1 acting in mammalian cells; a unique restriction enzyme site RE1 rarely existing in eukaryotic DNA and a transcription promoter PR2; a unique restriction enzyme site RE2 generating a 3'-protruding dG tail; a unique arbitrary restriction enzyme site RE3; a unique arbitrary restriction enzyme site RE4 generating a 3'-protruding terminus; a unique restriction enzyme site RE5 rarely existing in eukaryotic DNA and a transcription promoter PR3; and at least one kind of arbitrary restriction enzyme site RE6 generating a 3'-protruding terminus existing at an arbitrary position before the restriction site RE1; and further, at arbitrary positions other than the above-described restriction enzyme sites and promoters, an origin OR1 for replication in mammalian cells, an origin OR2 for replication of a single-stranded phage, an origin OR3 for replication in E. coli, and a selective marker.

6 Claims, 10 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "BstXI restriction site"

( i i i ) HYPOTHETICAL: NO ( i v ) ANTI-SENSE: NO ( i x ) FEATURE:
        ( A ) NAME/KEY: -
        ( B ) LOCATION: 1..12
        ( D ) OTHER INFORMATION: /note= "EITHER STRAND OF BstXI
            RESTRICTION SITE"

( x i ) SEQUENCE DESCRIPTION: SEQ ID NO:1:

CCANNNNNNT GG        1 2

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE L1"

( i i i ) HYPOTHETICAL: NO ( i v ) ANTI-SENSE: NO ( i x ) FEATURE:
        ( A ) NAME/KEY: -
        ( B ) LOCATION: 1..41
        ( D ) OTHER INFORMATION: /note= "OLIGONUCLEOTIDE PRIMER L1"

( x i ) SEQUENCE DESCRIPTION: SEQ ID NO:2:

AATTCCAGGG GGGTGGTGGA TATCCTGGTA CCGCGGCCGC G                                   4 1

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE PRIMER L2"

( i i i ) HYPOTHETICAL: NO ( i v ) ANTI-SENSE: NO ( i x ) FEATURE:
        ( A ) NAME/KEY: -
        ( B ) LOCATION: 1..41
        ( D ) OTHER INFORMATION: /note= "OLIGONUCLEOTIDE PRIMER L2"

( x i ) SEQUENCE DESCRIPTION: SEQ ID NO:3:

GATCCGCGGC CGCGGTACCA GGATATCCAC CACCCCCCTG G                                   4 1

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE PRIMER L3"

( i i i ) HYPOTHETICAL: NO ( i v ) ANTI-SENSE: NO ( i x ) FEATURE:
        ( A ) NAME/KEY: -
        ( B ) LOCATION: 1..23
        ( D ) OTHER INFORMATION: /note= "OLIGONUCLEOTIDE PRIMER L3"

( x i ) SEQUENCE DESCRIPTION: SEQ ID NO:4:

CCATGATTAC GTATTTAATA CGA                                                       2 3

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE PRIMER L4"

( i i i ) HYPOTHETICAL: NO ( i v ) ANTI-SENSE: NO ( i x ) FEATURE:
        ( A ) NAME/KEY: -
        ( B ) LOCATION: 1..25
        ( D ) OTHER INFORMATION: /note= "OLIGONUCLEOTIDE PRIMER L4"

( x i ) SEQUENCE DESCRIPTION: SEQ ID NO:5:

GATCTCCCTT TAGTGAGGGT TATTG                                                     2 5

( 2 ) INFORMATION FOR SEQ ID NO:6:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OLIGONUCLEOTIDE PRIMER L5"

( i i i ) HYPOTHETICAL: NO ( i v ) ANTI-SENSE: NO ( i x ) FEATURE:
    ( A ) NAME/KEY: -
    ( B ) LOCATION: 1..25
    ( D ) OTHER INFORMATION: /note= "OLIGONUCLEOTIDE PRIMER L5"

( x i ) SEQUENCE DESCRIPTION: SEQ ID NO:6:

GATCCAATAA CCCTCACTAA AGGGA         25

( 2 ) INFORMATION FOR SEQ ID NO:7:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OLIGONUCLEOTIDE PRIMER L6"

( i i i ) HYPOTHETICAL: NO ( i v ) ANTI-SENSE: NO ( i x ) FEATURE:
    ( A ) NAME/KEY: -
    ( B ) LOCATION: 1..28
    ( D ) OTHER INFORMATION: /note= "OLIGONUCLEOTIDE PRIMER L6"

( x i ) SEQUENCE DESCRIPTION: SEQ ID NO:7:

GCCTCGAGTG TAAAACGACG GCCAGTAC         28

( 2 ) INFORMATION FOR SEQ ID NO:8:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "OLIGONUCLEOTIDE PRIMER L7"

( i i i ) HYPOTHETICAL: NO ( i v ) ANTI-SENSE: NO ( i x ) FEATURE:
    ( A ) NAME/KEY: -
    ( B ) LOCATION: 1..28
    ( D ) OTHER INFORMATION: /note= "OLIGONUCLEOTIDE PRIMER L7"

( x i ) SEQUENCE DESCRIPTION: SEQ ID NO:8:

GTACTGGCCG TCGTTTTACA CTCGAGGC         28

( 2 ) INFORMATION FOR SEQ ID NO:9:

( i ) SEQUENCE CHARACTERISTICS:
    ( A ) LENGTH: 23 base pairs
    ( B ) TYPE: nucleic acid ( C ) STRANDEDNESS: single
            ( D ) TOPOLOGY: linear ( i i ) MOLECULE TYPE: other nucleic acid
            ( A ) DESCRIPTION: /desc = "OLIGONUCLEOTIDE PRIMER L8"

( i i i ) HYPOTHETICAL: NO ( i v ) ANTI-SENSE: NO ( i x ) FEATURE:
            ( A ) NAME/KEY: -
            ( B ) LOCATION: 1..23
            ( D ) OTHER INFORMATION: /note= "OLIGONUCLEOTIDE PRIMER L8"

( x i ) SEQUENCE DESCRIPTION: SEQ ID NO:9:

ACACAGGAAA CAGCTATGAC CAT                                                                23

( 2 ) INFORMATION FOR SEQ ID NO:10:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OLIGONUCLEOTIDE PRIMER L9"

( i i i ) HYPOTHETICAL: NO ( i v ) ANTI-SENSE: NO ( i x ) FEATURE:
            ( A ) NAME/KEY: -
            ( B ) LOCATION: 1..30
            ( D ) OTHER INFORMATION: /note= "OLIGONUCLEOTIDE PRIMER L9"

( x i ) SEQUENCE DESCRIPTION: SEQ ID NO:10:

GATCATGGTC ATAGCTGTTT CCTGTGTGAA                                                         30

( 2 ) INFORMATION FOR SEQ ID NO:11:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OLIGONUCLEOTIDE PRIMER L10"

( i i i ) HYPOTHETICAL: NO ( i v ) ANTI-SENSE: NO ( i x ) FEATURE:
            ( A ) NAME/KEY: -
            ( B ) LOCATION: 1..19
            ( D ) OTHER INFORMATION: /note= "OLIGONUCLEOTIDE PRIMER L10"

( x i ) SEQUENCE DESCRIPTION: SEQ ID NO:11:

AGCTAGGCCT ACATGGCCA                                                                     19

( 2 ) INFORMATION FOR SEQ ID NO:12:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "OLIGONUCLEOTIDE PRIMER L11"

( i i i ) HYPOTHETICAL: NO ( i v ) ANTI-SENSE: NO ( i x ) FEATURE:
  ( A ) NAME/KEY: -
  ( B ) LOCATION: 1..19
  ( D ) OTHER INFORMATION: /note= "OLIGONUCLEOTIDE PRIMER L11"

( x i ) SEQUENCE DESCRIPTION: SEQ ID NO:12:

```
AGCTTGGCCA TGTAGGCCT                                                      19
```

CLONING VECTOR PLASMID, VECTOR-PRIMER DERIVED THEREFROM AND PREPARATION METHOD OF CDNA BANK USING THE SAME

BACKGROUND OF THE INVENTION

I. Related Applications

This application is a divisional of application Ser. No. 08/466,111, filed on Jun. 6, 1995, now U.S. Pat. No. 5,624,826 which is a continuation application of Ser. No. 08/255,799 filed on Jun. 7, 1994, now abandoned, which is a continuation application of Ser. No. 08/115,796 filed on Sep. 3, 1993, now abandoned, which is a continuation application of Ser. No. 07/606,826 filed on Oct. 31, 1990, now abandoned, the entire contents of which are hereby incorporated by reference.

II. Field of the Invention

The present invention relates to a multi-functional cloning vector, a vector-primer derived therefrom, and a method to prepare a cDNA bank using the same. This invention provides a method to obtain readily a cDNA which can be used to produce a large amount of protein which is available as a medicine.

III. Description of the Related Art

Proteins constituting cells in our body play a central role to maintain our life as the skeleton of cells, catalysts of reactions, and mediators of signal transduction. Thus, finding new proteins and elucidating those structures and functions are important not only to know life but also to use proteins as medicines or reagents for diagnosis. Although there have been many trials to use these proteins functioning in our body as a medicine, few proteins have been available because of difficulty of preparing a large amount of protein. The recent progress of genetic engineering made it easy to find a gene encoding a useful protein from human cells and to express it in bacteria or animal cells in high yields. Using this technique recently many proteins were recently developed as medicines.

Any human protein has potential utility as a medicine because it functions in the body. It has been known that many genetic diseases are caused by disappearance of a protein playing an important role in a living cell. Therefore to produce a large amount of a protein and to elucidate its function and any relationship to disease are important steps for developing new medicines. If the investigation is begun from the purification of a protein showing a target activity, it takes a long time and much labor to obtain a large amount of starting material. To avoid this problem, the inventors take the strategy of analyzing the gene by which information of the amino acid sequence of a protein is encoded. In our plan, cDNA (complementary DNA) is synthesized from all mRNA which is transcribed from the genome and is translated into protein, and then each cDNA is characterized.

The number of genes in the human genome is estimated to be approximately $10^5$, which may correspond to the number of human proteins. Recently the determination of the whole sequence of the human genome is discussed around the world, under the rubric of the Human Genome Project. If this plan is realized, the amino acid sequence of all proteins encoded in the human genome is expected to be elucidated. It is, however, difficult to determine the amino acid sequence only from the nucleotide sequence of genomic DNA because the genome consists of exons encoding parts of proteins and introns not encoding protein. In the cell, MRNA transcribed from the genome is processed by deletion of introns and the processed mRNA containing only exons is translated into protein on ribosomes. Therefore if we determine the nucleotide sequence of the processed mRNA, we can obtain the information of the amino acid sequence of proteins encoded by the mRNA. The progress of gene recombination techniques enabled us to convert mRNA to cDNA and to introduce it into *E. coli*. According to this technique we can synthesize a "cDNA vector" which contains cDNA derived from one species of mRNA, and construct the "cDNA library" which is a group of *E. coli* containing cDNA vectors. If we determine the nucleotide sequence of all cDNAs contained in the cDNA library, which corresponds to the nucleotide sequences of all mRNA existing in a cell, we obtain the amino acid sequence of all proteins synthesized in a cell. We call the group of sequence-determined cDNAs the "cDNA bank ". If the obtained cDNA vector is introduced and expressed in adequate animal cells, the expression product may be used for a screening assay. Taking the above strategy, we can construct the cDNA bank of human proteins, which is called the "homo-protein" cDNA bank, in which the amino acid sequence of each cDNA has been determined and each cDNA can be expressed in mammalian cells. Here we describe only the case of human proteins as an example, but this strategy can apply to the case of other animal and plant cells, and we can obtain also useful information about proteins of these cells.

The success of above strategy depends on the quality of the cDNA library. From this point of view, there are many problems in cDNA libraries prepared by known methods, for example, that subcloning of a cDNA fragment into an adequate vector is required to sequence the cDNA, to screen to obtain a full-length cDNA using it as a probe, or to express it in animal cells. It takes a long time and much labor to analyze many cDNA clones by this subcloning procedure. This problem is solved by developing a novel method by which all of the above procedures can be carried out on the same vector. The minimum requirements for a cDNA vector satisfying the above method are 1) to contain a directional full-length cDNA clone, 2) to be sequenced easily, 3) to be used to prepare a probe which can be used for various screenings, and 4) to be expressed in in vivo or in vitro systems. The term "full-length cDNA clone" described in the requirement 1) means a cDNA clone containing at least the whole coding region of a protein encoded by an mRNA in this specification, but strictly the cDNA clone containing the whole sequence of a template mRNA from 5' end to poly A tail.

The most popular method to prepare cDNA at present is the so called Gubler-Hoffman method described below [Gene 25:263–269 (1983)]. The first strand of cDNA is synthesized from a poly(A)+RNA template isolated from cells and an oligo dT primer using reverse transcriptase. Then the RNA strand is replaced by a second DNA strand using *E. coli* RNase H, *E. coli* DNA polymerase I, and *E. coli* DNA ligase. After blunting both ends of the double-stranded cDNA by T4 DNA polymerase, an adequate oligonucleotide linker DNA is added. Then the resulting cDNA is ligated to a phage vector or a plasmid vector, and used to transform *E. coli*. It is difficult to obtain a full-length cDNA using this method, because when synthesizing a second strand, the 5' terminal sequence of mRNA used as a primer is deleted and both terminals of cDNA are often deleted by exonuclease activity of DNA polymerase I or T4 DNA polymerase. The vector containing an origin and a promoter for expression in mammalian cells, a replication origin of a single-stranded phage, and a RNA polymerase promoter, for example, such as pCDM8 [B.Seed, Nature 329:840–842 (1987)] is known. Using this vector, preparation of single-stranded DNA for sequencing, preparation of a RNA probe, synthesis of mRNA for in vitro or in vivo translation, and expression in a mammalian cell are possible, but the cDNA insertion is not directional. Thus, a cDNA library prepared using the Gubler-Hoffman method does not satisfy the requirement 1). Furthermore, the large size of pCDM8, which is 4.8 kbp long, is not suitable to clone a long cDNA.

The Okayama-Berg method [Mol. Cell. Biol. 2:161–170 (1982)] is known as a method giving full-length cDNA clones at high frequency, in which a dT-tailed vector-primer is used for synthesis of the first strand cDNA from poly(A) +RNA by reverse transcriptase. Following addition of a dC tail, dG-tailed linker DNA is ligated and then RNA is replaced by DNA by E. coli RNaseH, E. coli DNA polymerase I, and E. coli DNA ligase. Since the dC tail addition occurs rarely at the 3' end of a first strand cDNA incompletely extended, the dC-tailed clone gives a full-length cDNA preferentially. Using a vector-primer furthermore causes the directional insertion of cDNA. Okayama et al., [Mol. Cell. Biol. 3:280–289 (1983)] have developed an expression system in mammalian cells by using linker DNA containing an origin and a promoter of SV40. Honjo has developed an expression system in Xenopus oocytes for mRNA transcribed in vitro by using linker DNA containing a SP6 promoter [Japanese Patent 62-74291]. However, the use of the Okayama-Berg method is limited because to do so requires a high quality of technique. Also, the large number of dG residues in the tail at the 5' terminus often makes it difficult to sequence from the 5' terminus. It is further difficult to prepare probes by this method. Thus a cDNA library using this method does not satisfy the requirements 2) and 3) described above.

Although there have been several improved methods, no methods satisfy all four requirements described above. Since even the lack of one requirement makes it difficult to carry out the above strategy, the development of a method satisfying all of the above requirements is necessary.

SUMMARY OF THE INVENTION

It is therefore an object of the present invention to provide a method to construct a cDNA vector which satisfies the following four requirements, 1) to contain a directional full-length cDNA clone, 2) to be easily sequenced, 3) to be used to prepare an RNA probe which is complementary to a full-length cDNA and is used for screening, and 4) to be able to express the cDNA in a mammalian cell. The invention further includes a plasmid vector and a vector-primer derived from it, which is required for carrying out the above method.

The inventors succeeded in constructing a novel vector for cDNA cloning satisfying the above four requirements and to construct a human cDNA bank using it. The invention provides a cloning vector which comprises a promoter PR1 acting in mammalian cells, followed by a unique restriction enzyme site RE1 rarely existing in eukaryotic DNA and a transcription promoter PR2 followed by a unique restriction enzyme site RE2 generating a 3'-protruding dG tail, followed by a unique arbitrary restriction enzyme site RE3, followed by a unique arbitrary restriction enzyme site RE4 generating a 3'-protruding terminus, followed by a unique restriction enzyme site RE5 rarely existing in eukaryotic DNA and a transcription promoter PR3 and at least one kind of arbitrary restriction enzyme site RE6 generating a 3'-protruding terminus existing at an arbitrary position before the restriction site RE1, and further, at an arbitrary position except for the above regions, an origin OR1 for replication in mammalian cells, an origin OR2 for replication of a single-stranded phage, an origin OR3 for replication in E. coli, and a selective marker.

The invention further provides a vector-primer which is prepared from a cloning vector plasmid described above. After cutting a cloning vector at a restriction site RE4, the dT-tail is added by terminal deoxynucleotidyl transferase and then cut at the restriction site RE3.

The invention further provides a method to prepare a cDNA bank comprising cDNA vectors which contain sequence-determined cDNA inserts that can be expressed in mammalian cells. This method includes synthesizing cDNAs from poly(A)+RNA isolated from a cell using the vector-primer described above, transforming E. coli with them, preparing a cDNA plaque library by infection of a helper phage, and sequencing cDNA from the 5' terminal end using a single-stranded DNA isolated from a single-stranded phage plaque.

The invention further provides a method to prepare a library-specific cDNA bank including cDNA vectors which contain sequence-determined cDNA inserts and can be expressed in mammalian cells. This method comprises preparing two kinds of cDNA libraries LA and LB using the above method, preparing sense RNA probes from the library LA using RNA polymerase, preparing a group of anti-sense single-stranded cDNAs from the library LB, obtaining the library LA—specific cDNA clones by screening the library LA using probes which contain a hybridization mixture between RNA probes and single-stranded cDNAs prepared above, and sequencing them from the 5' terminus.

The invention enables us to obtain cDNA clones satisfying all four of the above requirements. Using this cloning vector, we can clone a full-length cDNA without a complicated procedure such as subcloning, determine its nucleotide sequence, prepare a complementary probe for screening, and express it in mammalian cells. Therefore this cloning vector is a powerful tool especially to prepare a cDNA bank originated from various mRNA. A "cDNA bank" in this specification means a cDNA library in which the nucleotide sequence of each cDNA clone has been already determined. Thus this invention enables us to determine the amino acid sequence of all proteins of a human or any other animal's cell in a shorter period than using conventional methods.

BRIEF DESCRIPTION OF THE DRAWINGS

FIG. 6 shows the construction of plasmid pTZ18RP4;

FIG. 7 shows the construction of plasmid pKAO;

FIG. 8 shows the construction of plasmid pKA1;

DETAILED DESCRIPTION OF THE PREFERRED EMBODIMENTS

Figure 1:
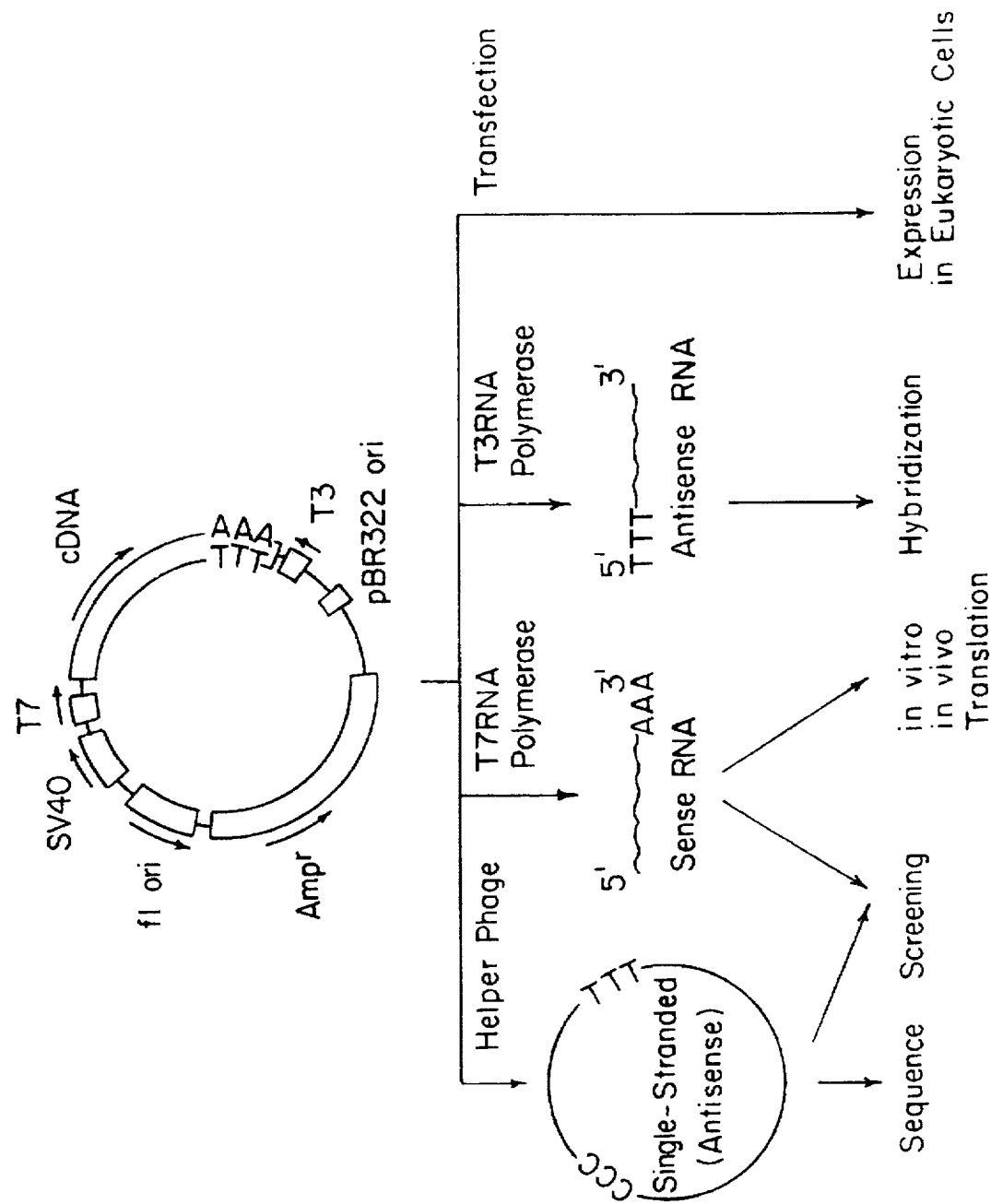
FIG. 1 shows the function of the cDNA vector of this invention.

FIG. 1 shows the functions of the cDNA vector of this invention. The construction method of a cloning vector, the preparation method of a cDNA vector using it, and examples showing that this cDNA vector satisfies above four requirements will now be described.

(1) Cloning Vector

The most characteristic point of this invention is the cloning vector used for cDNA synthesis. The vector-primer is used to satisfy the first one of the above four requirements and is endowed with multi-functional properties to satisfy the requirements 2), 3) and 4). As described above, the cloning vector included in this invention comprises a promoter PR1 acting in mammalian cells, followed by a unique restriction enzyme site RE1 rarely existing in eukaryotic DNA and a transcription promoter PR2, followed by a unique restriction enzyme site RE2 generating a 3'-protruding dG tail, followed by a unique arbitrary restriction enzyme site RE3, followed by a unique arbitrary restriction enzyme site RE4 generating a 3'-protruding terminus, followed by a unique restriction enzyme site RE5 rarely existing in eukaryotic DNA and a transcription promoter PR3 and at least one kind of arbitrary restriction enzyme site RE6 generating a 3'-protruding terminus existing at an arbitrary position before the restriction site RE1, and further, at an arbitrary position except for the above regions, an origin OR1 for replication in mammalian cells, an origin OR2 for replication of a single-stranded phage, an origin OR3 for replication in *E. coli*, and a selectable marker.

Figure 2:
FIG. 2 shows the arrangement of promoters in the cloning vector of this invention.

The term "unique" in the above description means that the restriction site appears only once on the plasmid. FIG. 2 shows the arrangement of promoters PR1, PR2, and PR3. A change of the order of RE1 and PR2 as well as the order of RE5 and PR3 is allowable. It is desirable that no extra nucleotide sequence exists between the restriction site and promoter. The restriction sites RE2, RE3, and RE4 are necessary to satisfy the requirement 1), OR2 and RE6 to satisfy the requirement 2), PR2, PR3, RE1, RE5, and OR2 to satisfy the requirement 3), and OR1 and PR1 to satisfy the requirement 4).

A promoter for expression in mammalian cells, PR1, includes promoters such as an early or late promoter of SV40, a late promoter of adenovirus 2, and a 5' long terminal repeat (LTR) of a retrovirus. A unique restriction enzyme site rarely existing in eukaryotic DNA, RE1 and RE5, includes restriction sites such as NotI, SnaBI, SfiI, and SpeI. A unique restriction enzyme site producing a 3'-protruding dG oligomer tail after digestion, RE2, includes restriction sites such as BstXI, SfiI, DraIII, and BglI. Since the nucleotide sequence of the cut site in these restriction enzyme sites can be replaced by any nucleotide pairs, if dG-dC is used as a nucleotide pair in them, cutting by these restriction enzymes produces a 3'-protruding dG terminus. For example, the nucleotide sequence of the restriction site for BstXI is shown below: (SEQ ID NO. 1)

5'-CCANNNNNNTGG-3'
3'-GGTNNNNNNACC-5'

If N is replaced in the top sequence by G, digestion of this site with BstXI produces the following terminal sequence.

5'-CCAGGGGG-3'
3'-GGTC-5'

Thus RE2 includes any kind of restriction sites which can produce a 3'-protruding terminus after restriction enzyme digestion, and so is not limited by the above examples.

RE6, which comprises at least one kind of arbitrary restriction enzyme site producing a 3'-protruding terminal existing at an arbitrary position before the restriction site RE1, includes any restriction site producing a 3'-protruding terminus as far as it is different from RE1, RE2, RE3, RE4, and RE5, and preferably is a site that exists rarely in eukaryotic DNA. One example is SfiI, but there are many other examples. It is desirable that RE6 contain more than two different restriction sites. It is not necessary that RE6 is a unique site but it is necessary that it exists upstream of RE1.

Transcription promoters PR2 and PR3 include promoters of polymerases such as T3 RNA polymerase, T7 RNA polymerase, and SP6 RNA polymerase. OR1 for a replication origin in mammalian cells includes an origin of SV40, for example. OR2 for a replication origin of a single-stranded phage includes origins of f1 phage or M13 phage. OR3 for a replication origin of *E. coli* includes origins of plasmids such as pBR322 or of the pUC series. A selective marker includes drug-resistance markers such as those for ampicillin, tetracycline, or kanamycin, and other markers such as for a nutrient requirement or temperature sensitivity. Although a neomycin-resistance gene can be introduced into this vector as a drug-resistance marker for a mammalian cell system, this may cause a disadvantage that the size of the vector becomes too long. It is further desirable to include a splicing junction and poly A addition signal sequence for high expression in mammalian cells.

A cDNA is introduced in a directional manner between the restriction sites RE2 and RE4, in which the 5'-terminal of the mRNA is adjacent to RE2. The direction of a replication origin of a single-stranded phage determines which of the double strands in the vector plasmid is produced as a single strand. In this vector system, the single-stranded DNA consists of an anti-sense strand for cDNA. In this specification, the strand possessing the same sequence as template mRNA except that U is replaced by T is defined as a sense strand, and the complementary sequence as an anti-sense strand.

To determine the nucleotide sequence from the 5' terminal of the cDNA, any synthetic oligonucleotide which anneals upstream of RE2 can be used as a sequencing primer. If the vector is designed to have the nucleotide sequences of primers used for sequencing of M13, these primers can be used for sequencing of a cDNA insert.

An RNA polymerase promoter PR2 is introduced into the vector in the direction producing a single-stranded RNA of the sense strand for a mRNA template. In the same manner, PR3 is introduced to produce an anti-sense strand. The plasmid described above can be readily constructed using known plasmids and synthetic oligonucleotides. The plasmid pKA1 described below as an example uses an early promoter of SV40 for PR1, SnaBI for RE1, T7 promoter for PR2, BstXI for RE2, EcoRV for RE3, KpnI for RE4, NotI for RE5, a T3 promoter for PR3, SfiI, PstI, and SphI for RE6, an origin of SV40 for OR1, an origin of phage f1 for OR2, an origin of pBR322 for OR3, an ampicillin resistant marker (β-lactamase gene) for a drug-resistance marker, and the nucleotide sequences of the universal and reverse primers of M13 phage for the priming site where a sequencing primer anneals, respectively. pKA1 further includes a 16S splicing site downstream of the SV40 promoter and a poly A addition signal sequence downstream of the T3 promoter. The size of pKA1 is 3.6 kbp and is shorter than known multi-functional cloning vectors. This makes it easy to get longer cDNA clones.

The plasmid described above is cut at restriction site RE4 to produce a 3'-protruding terminal, and then a dT tail is added to the terminal using terminal deoxynucleotidyl transferase. The desirable number of added dT residues is from 30 to 70, preferably from 50 to 60. Cutting at the restriction site RE3, the longer DNA fragment containing a vector is isolated by agarose gel electrophoresis and is used as a vector-primer.

(2) Method of Preparation of a cDNA Library

Figure 4:
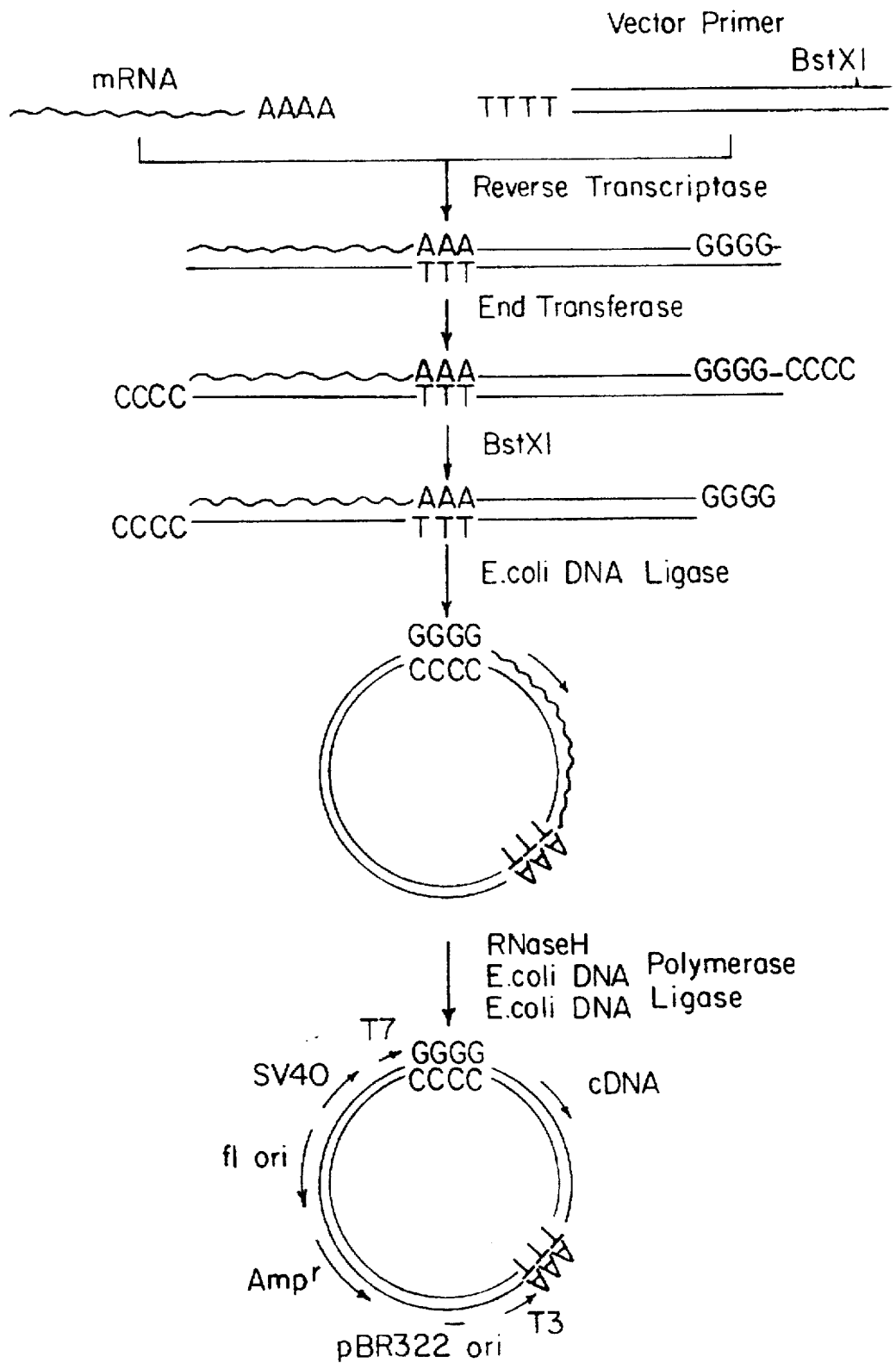
FIG. 4 shows the process to synthesize cDNA using the vector plasmid of this invention.

Poly(A)+RNA isolated from cells using a known method is annealed with a vector-primer described above, and then reverse transcriptase is used to synthesize the first strand of cDNA. The dC tail, the number of dC residues of which is preferably from 4 to 10, is added to the end of the first strand cDNA using terminal deoxynucleotidyl transferase. After cutting at the restriction site RE2, self-ligation is carried out using E. coli DNA ligase. Then the RNA strand is replaced by a second cDNA strand using E. coli RNase H, E. coli DNA polymerase I and E. coli DNA ligase. This procedure is shown in FIG. 4. The obtained ligation mixture containing cDNA-harboring plasmid is used to transform a host E. coli containing a F' factor. An E. coli strain containing a F' factor includes hosts such as MN522, JM101, JM103, JM105, JM109, AND DH5αF'. Transformants constituting a cDNA library are cultured and amplified in an appropriate medium such as L-broth or 2xTY containing ampicillin, if the vector has an ampicillin-resistance gene, and then are stocked in a deep freezer after adding glycerol or DMSO. If the culture of the cDNA library is infected with a helper phage, each E. coli cell releases into a medium a phage containing a single-stranded cDNA derived from a cDNA vector. This single-stranded cDNA has an anti-sense strand for a mRNA template. After infection of the cDNA library with helper phage and incubation, the E. coli cells are harvested, washed thoroughly with medium to remove helper phage, and diluted with medium. This diluted cell solution is mixed with a soft agar or a soft agarose solution containing E. coli host not harboring a cDNA vector, and the mixture is poured onto agar plates. After incubation, plaques can be seen where cDNA-harboring cells exist. E. coli cells picked up from a single plaque by a toothpick are cultured in a liquid medium such as 2xTY. A part of the culture medium is stored in a freezer. After the remaining culture is centrifuged, the cell pellet is used to isolate plasmid and the supernatant is used to isolate phage from which a single-stranded cDNA is isolated by known methods. It is desirable that a part of the supernatant containing phage is stored in a refrigerator. A helper phage used above includes phages such as M13K07 [J. Vieira and J. Messing, "Methods in Enzymology" vol. 153, p. 3, 1987], VCS-M13, and R408 (both can be purchased from Stratagene).

We can select an alternative procedure to isolate a single-stranded DNA, in which a single colony is picked up and incubated, and then infected with helper phage.

Using the above method, various types of cDNA libraries can be prepared, such as transformants containing cDNA vectors originated from a single species of mRNA, cDNA vectors as a double-stranded DNA, cDNA vectors as a single-stranded DNA, and phages containing a single-stranded DNA.

(3) Determination of nucleotide sequence

Either a single-stranded DNA or a double-stranded DNA can be used. A single-stranded DNA is preferred because more nucleotide sequences can be read. The nucleotide sequence can be determined using a dideoxy method in which a synthetic oligonucleotide 17 mer to 20 mer corresponding to the nucleotide sequence just before the restriction site RE2 is used as a sequencing primer and substrates labeled with a radioisotope or fluorescent dye are used. A sequencing reaction is carried out using enzymes such as Klenow fragment, Taq DNA polymerase, T7 DNA polymerase, and reverse transcriptase. Using pKA1, a universal primer can be used for M13 sequencing, by which approximately 400 nucleotides from the 5'-terminal of a cDNA can be determined. If the cDNA is a full-length clone, an initiation codon followed by an open reading frame in the determined sequence may be found. If no stop codon appears within the open reading frame, it is necessary to determine further sequence, in which case a new primer corresponding to the nucleotide sequence near the 3'-end of the determined sequence should be synthesized to be used for further sequencing. Using the plasmid of the present invention, derivatives deleted from a 5' terminal of a CDNA insert can be prepared by cutting the cDNA-harboring plasmid at restriction sites RE1 and RE6 followed by exonuclease treatment according to the known deletion method. These derivatives can be used to determine the nucleotide sequence using a primer corresponding to the nucleotide sequence just before the restriction site RE6, which corresponds to the reverse primer for M13 in the case of the pKA1 system.

Since the obtained nucleotide sequence corresponds to the sequence of a sense strand which is the same as the sequence of mRNA, this sequence can be used to search similarity to known sequences in a database: a DNA database for a nucleotide sequence and a protein database for an amino acid sequence of an open reading frame. If there is similarity to a known sequence, the function and characteristics of the protein encoded by the obtained cDNA can be estimated.

(4) Screening Method

When determination of sequences of all cDNA clones included in the library is desired, it is desirable to remove the already sequenced clones from the library to avoid the overlapped sequencing of the same clone. This invention provides a subtraction method satisfying the above demand. This method also can be used to obtain cell-specific clones or stimulus-induced clones.

An example that a cDNA library LA is subtracted by a cDNA library LB will now be described. This case corresponds to one in which a library LA contains novel clones or specific clones, on the other hand, a library LB contains sequence-determined clones or common clones. The library LA is cultured and amplified, and total plasmids containing cDNA vectors are isolated, which are cut at the restriction site RE5 and then reacted with the RNA polymerase acting on a promoter site PR2. If a substrate nucleotide labeled with a radioisotope or fluorescent dye is added in the reaction mixture, labeled RNA corresponding to the sense strand for each cDNA is obtained. On the other hand, the library LB is cultured and infected by a helper phage to prepare a single-stranded DNA from the supernatant. When the labeled RNAs prepared from library LA and the single-stranded DNA prepared from library LB are mixed and hybridized, the sense RNA strand hybridizes with the corresponding anti-sense single-stranded DNA derived from the common cDNA clones existing in both libraries, but labeled RNAs derived from specific cDNA clones in the library LA remain free. If the hybridization mixture is used as a probe to screen a library LA by the methods of plaque hybridization or colony hybridization, specific clones existing only in the library LA can be obtained. The principle of the subtraction method described above is shown in FIG. 5.

Since the cDNA vector described in this invention has a transcription promoter PR3 after the 3' terminal of the cDNA, an RNA probe which consists of an antisense strand for cDNA can be prepared by cutting the cDNA vector at the restriction site RE1 and reacting with an RNA polymerase acting on PR3. The product can be used as a probe for Northern hybridization.

(5) Expression in animal cells

Since the cDNA vector described in this invention has a replication origin and promoter functioning in mammalian cells, this can be used to express the inserted cDNA in mammalian cells if the isolated CDNA-harboring plasmid is introduced into cells by using known methods such as a calcium phosphate method or an electroporation method. If the introduced cDNA encodes a receptor protein or a secreted protein, this method can be used for an expression screening.

By cutting at the restriction site RE5 and reacting it with a CAP-like nucleotide substrate such as m$^7$GpppG and RNA polymerase acting on PR2, RNA which is useful in in vitro or Xenopus oocyte translation systems can be obtained.

The present invention will now be described by way of examples, but various changes and modifications can be made without departing from the invention.

The basic procedures of DNA recombination and the reaction conditions were in accordance with the literature [T. Maniatis et al. (1982), "Molecular Cloning. A Laboratory Manual," Cold Spring Harbor Laboratory].

EXAMPLE 1

Construction of Cloning Vector pKA1

Figure 6:
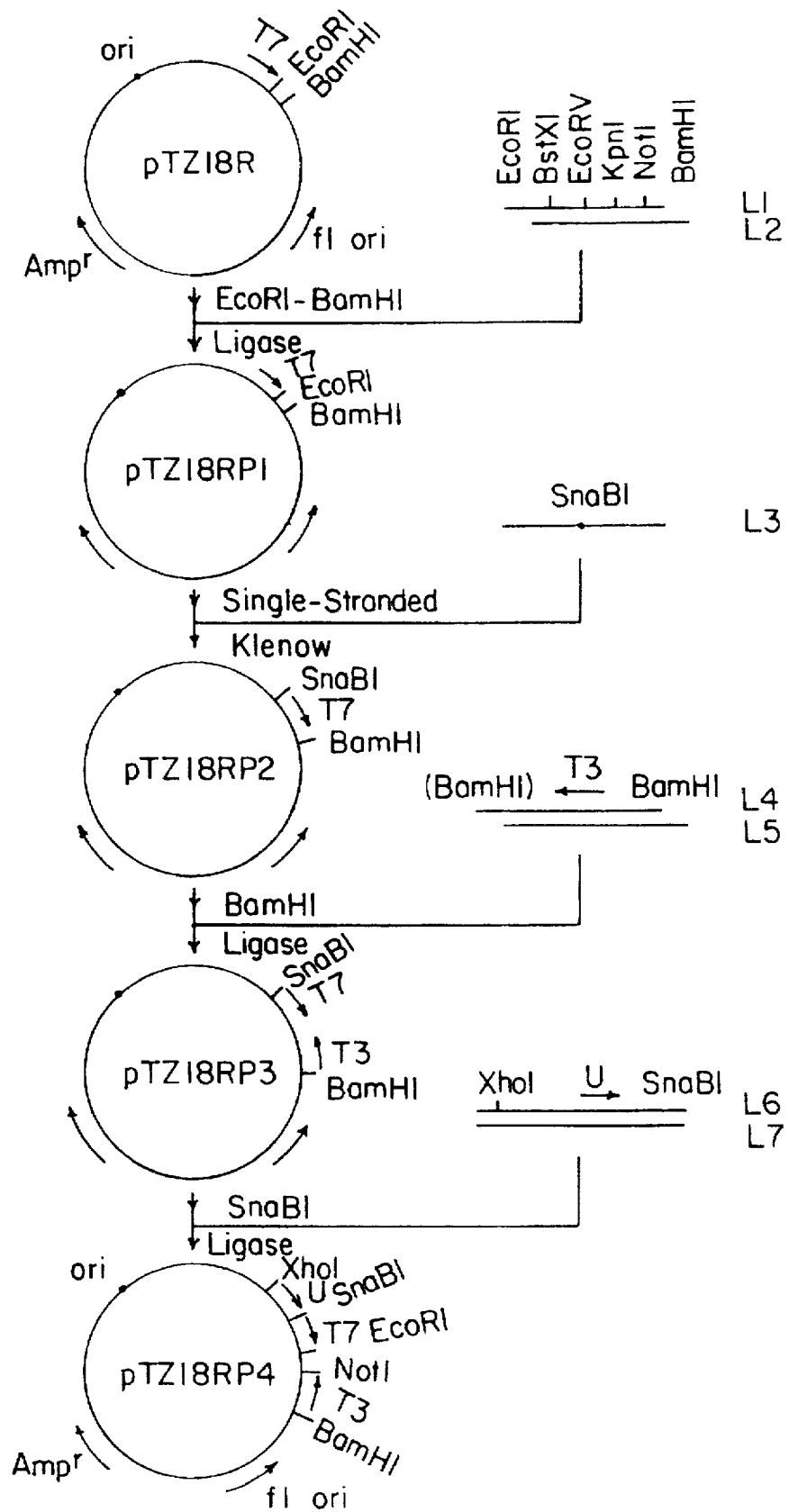
FIGS. 6 to 8 show the procedures to construct the vectors of this invention.

(1) Preparation of pTZ18RP1 (FIG. 6)

Ten μg of the plasmid pTZ18RP1 purchased from Pharmacia were digested with 100 units of BamHI and 100 units of EcoRI. The reaction mixture was fractionated by 0.8% agarose gel electrophoresis (AGE), and then a DNA fragment of 2.9 kbp was isolated from the gel. Ten pmoles of synthetic oligomers L1 and L2 (SEQ. ID. Nos. 2 and 3, respectively), which contain the restriction enzyme sites EcoRI, BstXI, EcoRV, KpnI, NotI, and BamHI, were annealed and ligated to the above DNA fragment.

L1 5'-AATTCCAGGGGGGTGGTGGATATCCTGGTAC-CGCGGCCGCG-3' (SEQ ID. No. 2)

L2 3'GGTCCCCCCACCACCTATAGGACCATG-GCGCCGGCGCCTAG'5' (SEQ ID. NO. 3)

*E. coli* HB101 was transformed with the ligation mixture and plasmids were isolated from several transformants. The insertion site of the synthetic oligomer into the plasmids was sequenced using a reverse primer for M13 sequencing. The plasmid possessing the designed sequence was denoted pTZ18RP1.

(2) Preparation of pTZ18RP2 (FIG. 6)

A SnaBI site was introduced before a T7 promoter using site-directed mutagenesis. A transformant of *E. coli* CJ236 (purchased from BioRad) by the plasmid pTZ18RP1 prepared in section (1) was cultured in 5 ml of 2xTY medium containing 50 μg/ml of ampicillin at 37° C. for one hour. Then a helper phage M13KO7 (purchased from Pharmacia) solution was added and cultured at 37° C. overnight. A single-stranded DNA (ssDNA) was isolated from the culture medium. The ssDNA annealed with 10 pmoles of synthetic oligomer L3 (SEQ ID. NO. 4) in which the 5' terminal was phosphorylated by T4 polynucleotide kinase was mixed with 4 units of Klenow fragment, 350 units of T4 DNA ligase, and 0.8 mM of dNTPs followed by incubation at 4° C. for 5 minutes, at room temperature for 5 minutes, and finally at 37° C. for 2 hours.

L3 5'-CCATGATTACGTATTTAATACGA-3' (SEQ. ID. NO. 4)

*E. coli* JM109 was transformed with the ligation mixture and plasmids were isolated from several transformants. The plasmid which could be cut by SnaBI and possesses the designed sequence was denoted by pTZ18RP2.

(3) Preparation of pTZ18RP3 (FIG. 6)

A T3 promoter was introduced into the BamHI site in pTZ18RP2. Ten μg of pTZ18RP2 prepared in section (2) were digested with 100 units of BamHI. After the reaction mixture was fractionated by 0.8% agarose gel electrophoresis, a DNA fragment was isolated from the gel. Ten pmoles of synthetic oligomers L4 and L5 (SEQ. ID. NOs. 5 and 6, respectively) containing a T3 promoter were annealed and ligated to the above DNA fragment.

L4 5'-GATCTCCCTTTAGTGAGGGTTATTG-3' (SEQ. ID. NO. 5)

L5 3'-AGGGAAATCACTCCCAATAACCTAG-5' (SEQ. ID. NO. 6)

*E. coli* NM522 was transformed with the ligation mixture and plasmids were isolated from several transformants. A plasmid possessing the designed sequence was denoted pTZ18RP3.

(4) Preparation of pTZ18RP4 (FIG. 6)

The XhoI site and universal primer sequence (designated by U) for M13 sequencing was introduced into the SnaBI site in pTZ18RP3. Ten μg of pTZ18RP3 prepared in section (3) were digested with 100 units of SnaBI. After the reaction mixture was fractionated by 0.8% agarose gel electrophoresis, a DNA fragment was isolated from the gel. Ten pmoles of synthetic oligomers L6 and L7 (SEQ. ID. NOs. 7 and 8, respectively) containing a XhoI site and a universal primer sequence (designated by U) for M13 sequencing were annealed and ligated to the above DNA fragment.

L6 5'-GCCTCGAGTGTAAAACGACGGCCAGTAC-3' (SEQ. ID. NO. 7)

L7 3'-CGGAGCTCACATTTTGCTGCCGGTCATG-5' (SEQ. ID. NO. 8)

*E coli* NM522 (purchased from Stratagene) was transformed with the ligation mixture and plasmids were isolated from several transformants. A plasmid possessing the designed sequence was denoted pTZ18RP4.

Figure 7:
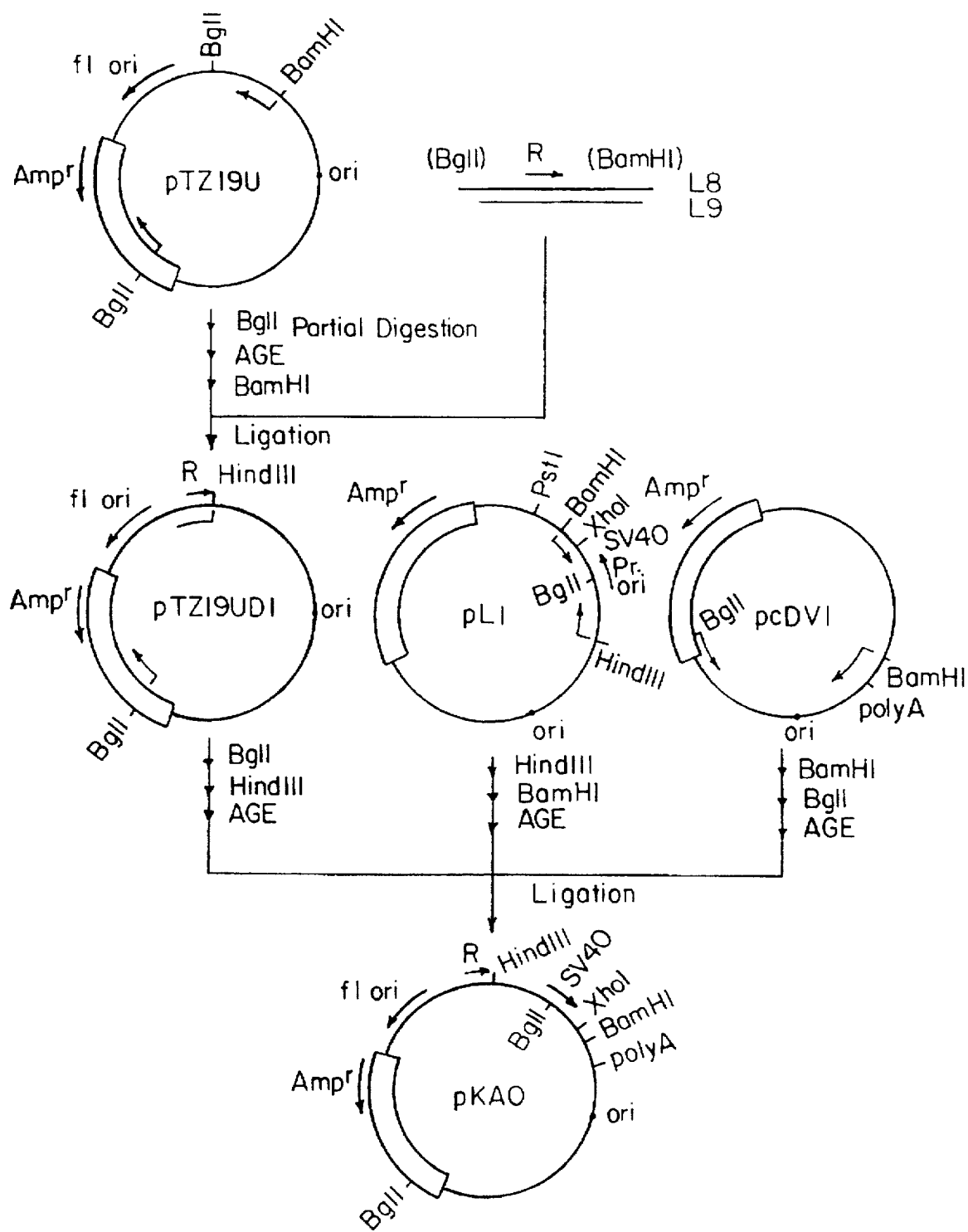

(5) Preparation of pTZ19UD1 (FIG. 7)

A reverse primer sequence (designated by R) for M13 sequencing was introduced between the BglI and BamHI sites in the plasmid pTZ19U. Two μg of pTZ19U (purchased from Toyobo) were partially digested with 20 units of BglI at 37° C. for 15 minutes. A fragment of 2.8 kbp cut at one site was isolated from the gel after fractionation by 1.2% agarose gel electrophoresis. After this fragment was digested with 100 units of BamHI, a fragment of 2.7 kbp was isolated by 1.2% agarose gel electrophoresis. Ten pmoles of synthetic oligomers L8 and L9 (SEQ. ID. NOs. 9 and 10, respectively) containing a reverse primer sequence (designated by R) for M13 sequencing were annealed and ligated to the BamHI-BglI fragment of pTZ19U.

L8 5'-ACACAGGAAACAGCTATGACCAT-3' (SEQ. ID. NO. 9)

L9 3'-AAGTGTGTCCTTTGTCGATACTGGTACTAG-5' (SEQ. ID. NO. 10)

*E. coli* JM109 was transformed with the ligation mixture and plasmids were isolated from several transformants. A plasmid possessing the designed sequence was denoted pTZ19UD1.

(6) Preparation of pKAO FIG. 7)

Ten μg of pTZ19UD1 prepared in section (5) were digested with 100 units of BglI and 100 units of HindIII. After fractionation by 1.2% agarose gel electrophoresis, a 1.4 kbp fragment containing a fl origin was isolated from the gel. Ten μg of pL1 (purchased from Pharmacia) were digested with 100 units of HindIII and 100 units of BamHI. After fractionation by 1.8% agarose gel electrophoresis, a 420 bp fragment containing an origin and early promoter of SV40 was isolated from the gel. Ten µg of pcDVI (purchased from Pharmacia) were digested with 100 units of BamHI and 100 units of BglI. After fractionation by 0.8% agarose gel electrophoresis, a 1.6 kbp fragment containing a poly A addition signal sequence was isolated from the gel. These three fragments were ligated and then *E. coli* HB101 was transformed with the ligation mixture. Plasmids were isolated from several transformants and digested with BamHI, BglI and HindIII to confirm that the restriction map of the obtained plasmid agrees with that of pKAO.

Figure 8:
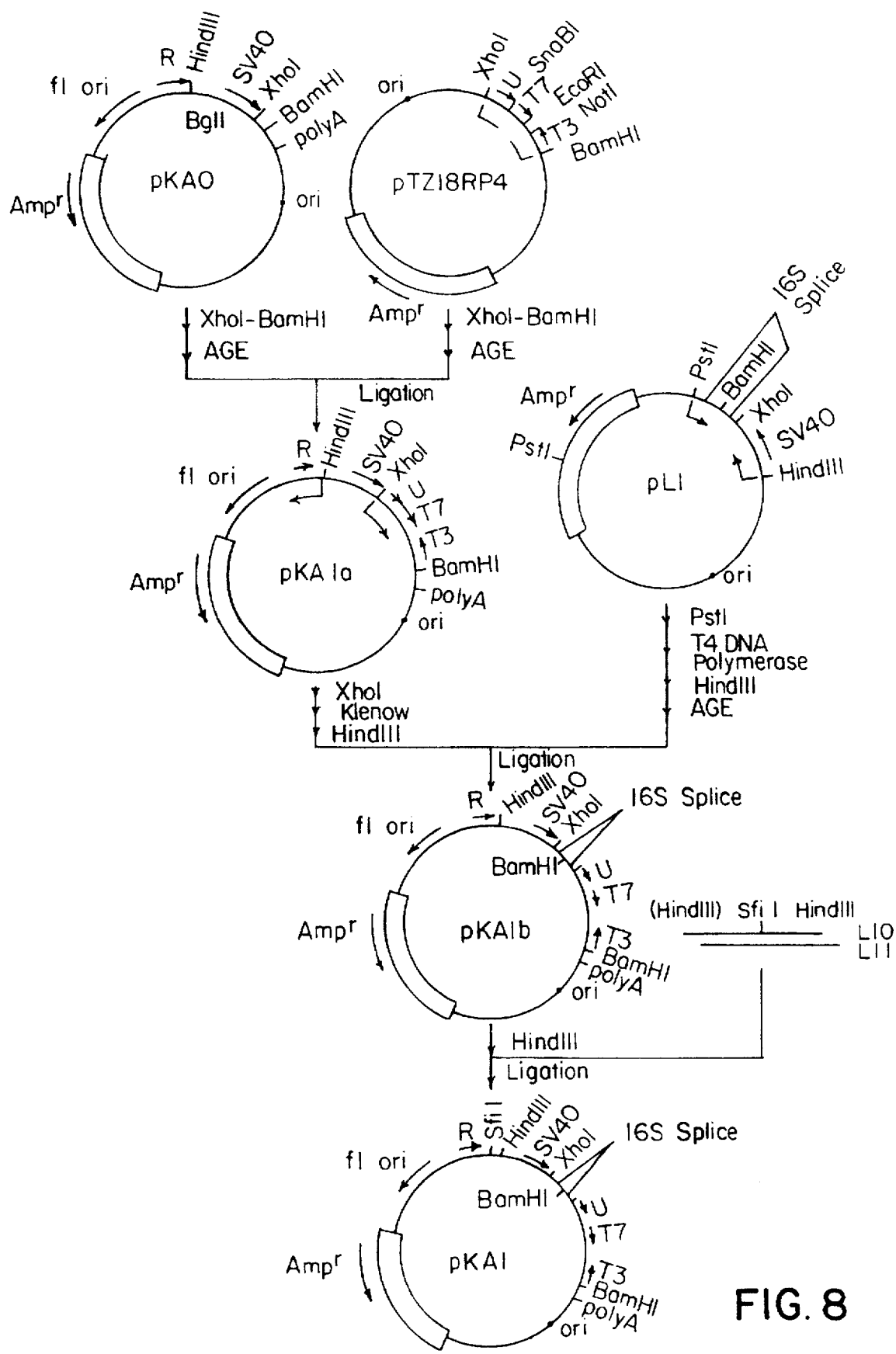

(7) Preparation of pKA1a (FIG. 8)

After 10 µg of pTZ18RP4 prepared in section (4) were digested with 100 units of BamHI and 100 units of XhoI a fragment of 117 bp was isolated by 1.8% agarose gel electrophoresis. On the other hand, after 10 µg of pKAO prepared in section (6) were digested with 100 units of BamHI and 100 units of XhoI, a fragment of 3.3 kbp was isolated by 0.8% agarose gel electrophoresis. Both fragments were ligated and then *E. coli* HB101 was transformed with the ligation mixture. Plasmids were isolated from several transformants and digested with BamHI and XhoI to confirm that the restriction map of the obtained plasmid agrees with that of pKA1a.

(8) Preparation of pKA1b (FIG. 8)

Ten µg of pL1 were digested with 100 units of PstI, and the terminals were blunted with T4 DNA polymerase. After this fragment was digested with HindIII, a 500 bp fragment containing a SV40 promoter and 16S splicing site was isolated by 1.8% agarose gel electrophoresis.

One µg of pKA1a was digested with 100 units of XhoI and the terminals were blunted by Klenow fragment. After this fragment was digested with HindIII, a fragment of 3 kbp was isolated by 0.8% agarose gel electrophoresis.

Both fragments were ligated and then *E. coli* HB101 was transformed with the ligation mixture. Plasmids were isolated from several transformants and digested with HindIII and BamHI to confirm that the restriction map of the obtained plasmid agrees with that of pKA1b.

(9) Preparation of pKA1 (FIG. 8)

After 10 µg of pKA1b were digested with 100 units of HindIII, a fragment of 3.6 kbp was isolated by 1.8% agarose gel electrophoresis. Ten pmoles of synthetic oligomers L10 and L11 (SEQ. ID. NOs. 11 and 12, respectively) containing a restriction site SfiI were annealed and ligated to the above fragment.

L10 5'-AGCTAGGCCTACATGGCCA-3' (SEQ. ID. NO. 11)

L11 3'-TCCGGATGTACCGGTTCGA-5' (SEQ. ID. NO. 12)

Figure 3:
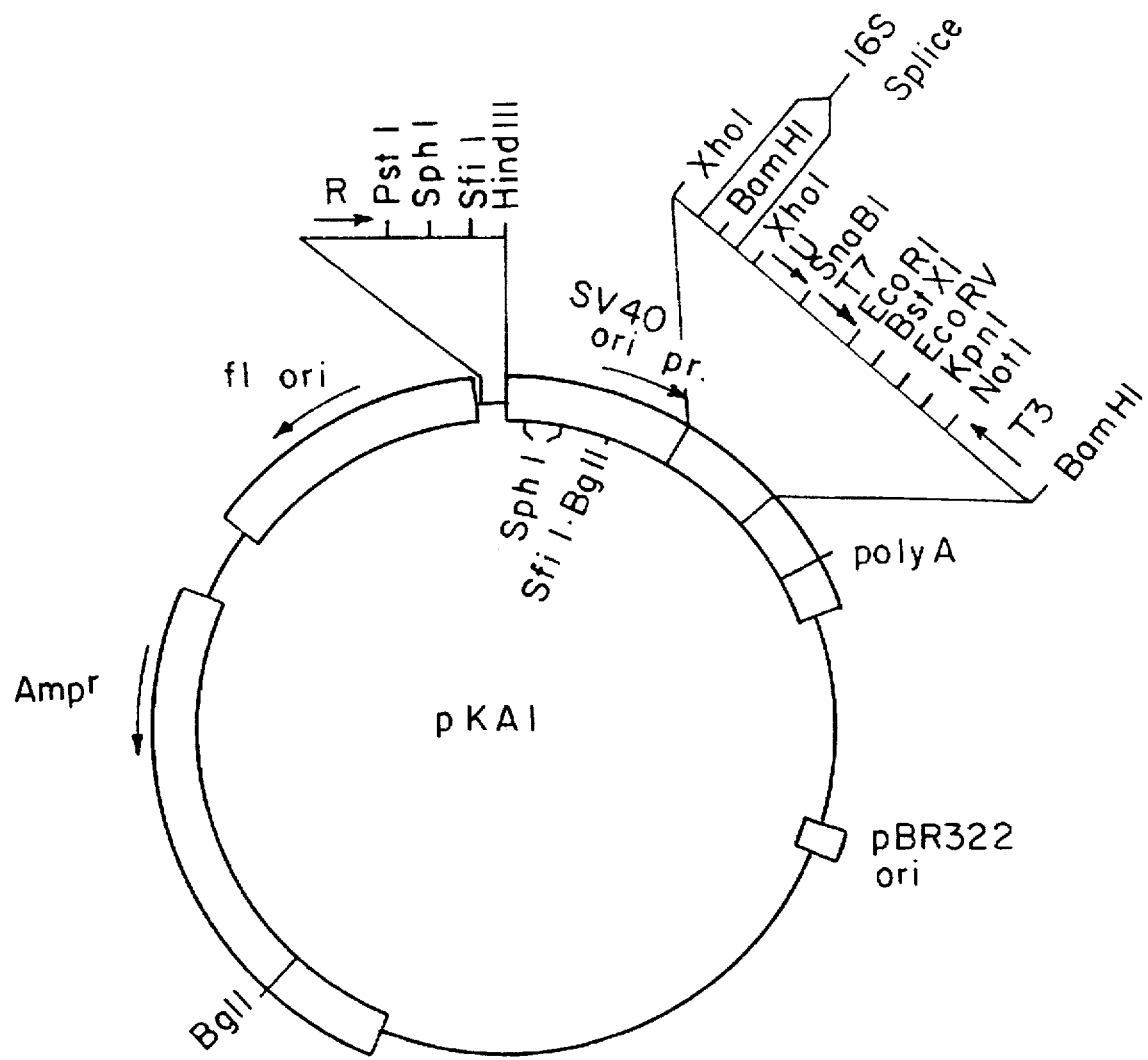
FIG. 3 shows the restriction map of the vector pKA1 of this invention.

*E. coli* HB101 was transformed with the ligation mixture and plasmids were isolated from several transformants. After the insertion site of the oligomers was sequenced using a reverse primer for M13 sequencing, the plasmid possessing the designed sequence, in which the order of restriction sites is SphI-SfiI-HindIII, was denoted pKA1. The details of restriction map of pKA1 are shown in FIG. 3.

EXAMPLE 2

Figure 9:
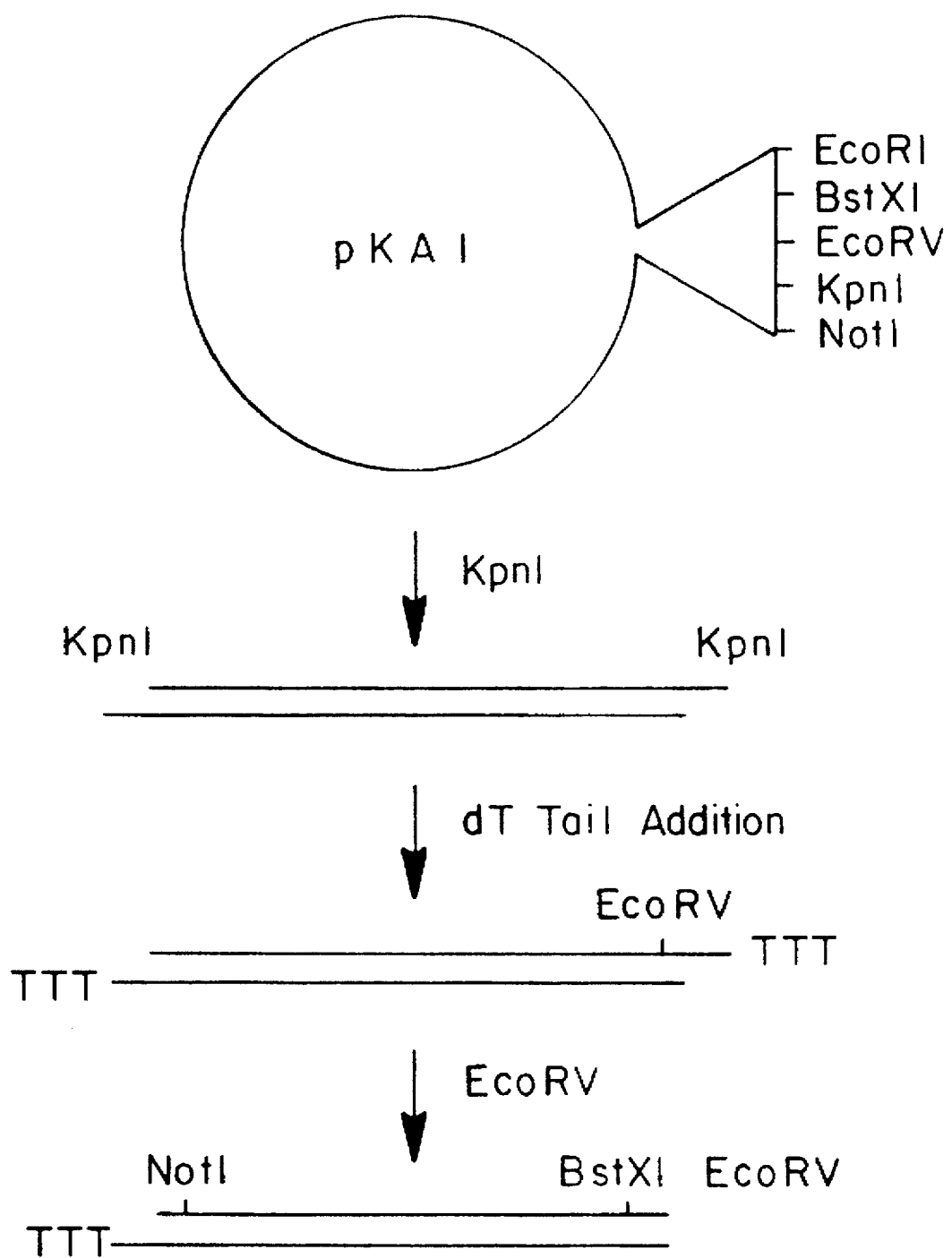
FIG. 9 shows the method to prepare the vector-primer of this invention.

Preparation of cDNA Library (1) Preparation of vector-primer (FIG. 9)

After 100 µg of PKA1 were digested with 200 units of KpnI, a fragment was isolated by 1.8% agarose gel electrophoresis. 70 µg of the isolated fragment were incubated at 37° C. for 30 minutes in a reaction mixture containing 20 µM of dTTP and 375 units of terminal deoxynucleotidyl transferase (purchased from Takara Shuzo). The number of tailed dT bases was estimated to be approximately 60, which was calculated from the uptake of [$\alpha$-$^{32}$p] dTTP added to a part of the reaction mixture. After digestion with EcoRV and fractionation by 0.8% agarose gel electrophoresis, a longer fragment was isolated and used as a vector-primer.

(2) Preparation of poly(a)$^+$RNA

Total mRNA was isolated using a guanidinium/thiocyanate method from a cell culture of human cell lines such as HUT-78, HUT-102, U937, and HT-1080. Poly(A)$^+$ RNA was purified from this mRNA using an oligo dT column.

(3) Synthesis of cDNA

The total process of cDNA synthesis is shown in FIG. 4. The reaction conditions described in the protocol of the Okayama-Berg method were used. Enzymes were purchased from Takara Shuzo. Briefly, after annealing 3 µg of poly(A) $^+$RNA prepared in section (2) with 1.5 µg of vector-primer prepared in section (1), reverse transcriptase was added to synthesize the first cDNA strand. The reaction mixture was extracted with phenol, and then the cDNA was precipitated by adding ethanol. The precipitate was dissolved in a reaction solution containing 1 µM of dCTP and reacted with 15 units of terminal deoxynucleotidyl transferase to add a dC tail. After phenol extraction and ethanol precipitation of the reaction mixture, the product was digested with 50 units of BstXI (purchased from New England Biolabs). After phenol extraction and ethanol precipitation of the reaction mixture, the product was annealed and self-ligated using *E. coli* DNA ligase. Then by adding dNTPs including dATP, dGTP, dCTP, and dTPP. *E. coli* DNA polymerase I and *E. coli* RNase H, the RNA strands were replaced by DNA strands.

(4) Preparation of cDNA library

*E. coli* NM522 was transformed with the solution containing cDNA vectors prepared in section (3). Transformants were suspended in 2xTY medium containing 100 µg/ml of ampicillin and incubated at 37° C. overnight. A part of the transformants was spread over an agar plate and incubated overnight. The number of independent clones included in the library was estimated, by counting the number of colonies appearing on the agar plate, to be approximately $2 \times 10^5 \sim 10^6$. A part of the culture was infected with helper phage M13KO7 (purchased from Pharmacia) and incubated at 37° C. overnight after adding kanamycin to 70 µg/ml. A part of the resulting culture was stocked at −80° C. as a 15% glycerol solution.

(5) Isolation of cDNA vector plasmid

The *E. coli* culture consisting of the cDNA library prepared in section (4) was harvested by centrifugation. The resulting pellet was washed thoroughly with 2 xTY medium, mixed with a culture of *E. coli* NM522 and a soft agar medium kept warm at 37° C., and poured onto 2 x TY agar plates. After incubation at 37° C. overnight, a single plaque appearing on the plates was isolated, suspended in 2x TY medium, and inoculated at 37° C. overnight. The culture was separated into the cell pellet and the supernatant by centrifugation. A double-stranded plasmid was isolated from the cell pellet, and a single-stranded DNA from the supernatant. The overall cultures were stocked at −80° C. as a 15% glycerol solution, the double-stranded plasmid and the single-stranded DNA were stocked at −20° C. as a TE solution, and the culture supernatant was stocked at 4° C. in a refrigerator.

EXAMPLE 3

Preparation of Human cDNA Bank (1) Size determination of human cDNA insert

The double-stranded plasmids isolated in section (5) of Example 2 were digested with EcoRI and NotI. The size of the resulting cDNA fragment was determined by 0.8% agarose gel electrophoresis.

(2) Determination of nucleotide sequence

The determination of the nucleotide sequence of a single-stranded cDNA prepared in section (5) of Example 2 was carried out using a DNA sequencer (purchased from Applied Biosystems). The sequencing reaction was performed by the dideoxy method using a fluorescent-labeled universal primer for M13 sequencing and Taq polymerase. This method could provide the nucleotide sequence of approximately 400 bp from the 5' end of a cDNA. We found 4~10 tails of dG at the 5' end of the cDNA. The obtained nucleotide sequences were filed on the disk of a computer as the "Homo-Protein cDNA database."

(3) Analysis of nucleotide sequence

The filed nucleotide sequences were analyzed using computer software including the genetic information analysis system GENIAS and the protein information analysis system PRINAS (both purchased from Mitsui Knowledge Industry). First, a homology search was carried out using each nucleotide sequence and the DNA database "Gen-Bank®." Then whether an initiation codon and an open reading frame of an amino acid sequence converted from the nucleotide sequence exists was investigated. If an open reading frame existed, a homology search of the amino acid sequence was carried out using the protein database "PRI-NAS."

Using the above method a cDNA bank, that is, the group of cDNA vectors in which the size of cDNA insert, the nucleotide sequence from 5' end, and the amino acid sequence encoded by the open reading frame were determined, was constructed. So far 20% of analyzed clones have an open reading frame which sequence has a similarity with the amino acid sequence of a known protein in the database. Most of the cDNA inserts are full-length clones. The obtained clones include a wide variety of proteins such as metabolic enzymes, proteins having a role in DNA replication or protein synthesis, secreted proteins, and extracellular matrix. Table 1 shows the examples of clones encoding proteins which have a similarity with a known protein.

EXAMPLE 4

Plaque Hybridization Using RNA Probe (1) Preparation of RNA probe

An RNA probe was prepared using a kit purchased from Stratagene. Briefly, after the double-stranded cDNA vector plasmid was cut with NotI, the product was reacted in a reaction mixture containing 50 µCi of [α-$^{32}$P] CTP and T7 RNA polymerase to synthesize an RNA probe corresponding to the sense strand of cDNA.

(2) Plaque Hybridization

Figures 10A, 10B:
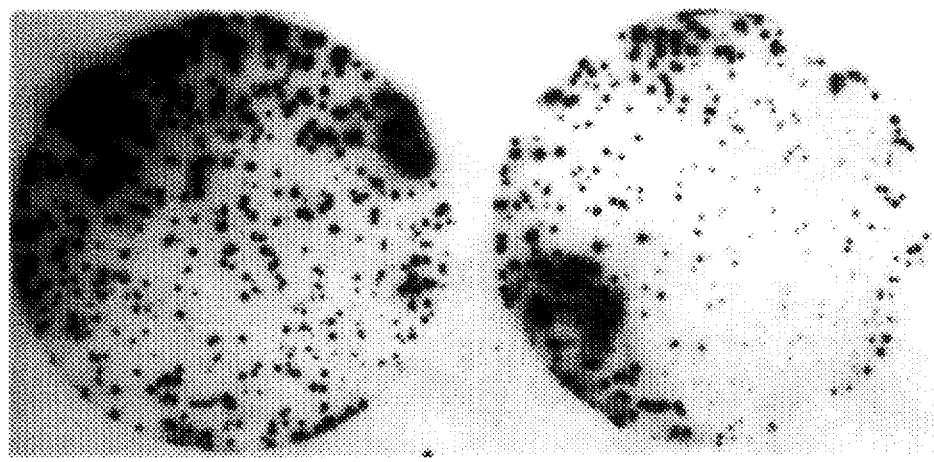
FIGS. 10A and 10B show the results of plaque hybridization and subtraction using the protocol according to this invention.

A cDNA plaque library was formed on agar plates using the method described in section (5) of Example 2. Dry nitrocellulose filters were placed on the surface of the agar plates to transfer phages existing around the plaque. In the same way, two replica filters were prepared. The filters were air-dried, and baked at 80° C. for 3 hours. The filters were preincubated at 37° C. for 2 hours in a solution containing 50% formamide, 5 x SSC, 10 x Denhardt's solution, and 0.1% SDS. After adding the RNA probe prepared in section (1), the incubation was sustained at 37° C. for 16 hours. The filters were washed with a solution containing 0.2 x SSC and 0.1% SDS at 65° C. for 1 hour, and air-dried. The resulting filters were subjected to autoradiography. FIG. 10A shows the result of a model experiment using a plasmid vector containing an actin cDNA. We can see positive signals where plaques exist.

(3) Subtraction method

Figure 5:
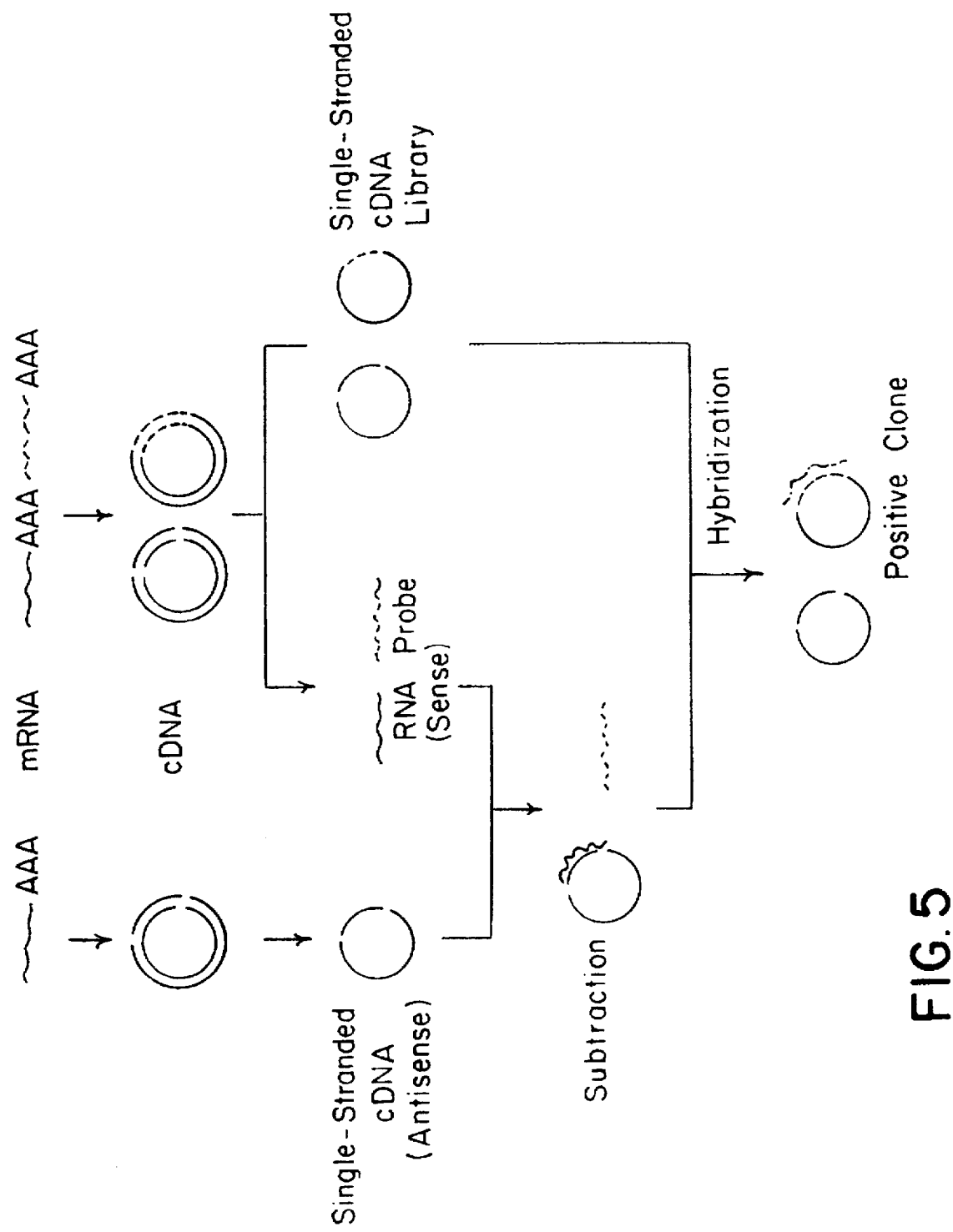
FIG. 5 shows the subtraction method using the cDNA system according to this invention.

An RNA probe and a single-stranded DNA were prepared from the clone containing an actin cDNA, and prehybridized. The resulting mixture was used as a probe for hybridization with a filter spotted with phage containing a single-stranded actin cDNA. As shown in FIG. 10B, we can see no positive signal on the autoradiogram. This means that a single-stranded DNA can inhibit completely the probe function of a corresponding RNA by prehybridization, thus that the subtraction method shown in FIG. 5 is possible.

EXAMPLE 5

Determination of Whole Nucleotide Sequence of cDNA Insert Using the Deletion Method The plasmid pKATNF1 was isolated from the clone No. 16 shown in Table 1 that contains the cDNA encoding TNF (Tumor Necrosis Factor). Fifteen µg of this plasmid were digested with 20 units of SphI and then with 15 units of SnaBI. After treatment with exonuclease III at 37° C., sampling was carried out at 1 minute intervals. These samples were mixed, treated with mung-bean nuclease and Klenow fragment, and then self-ligated to obtain plasmids deleted from the 5' terminal of the cDNA insert. The above reaction was carried out using a kilo-deletion kit purchased from Takara Shuzo. Single-stranded DNA was prepared from each deleted clone using the method described in sections (4) and (5) of Example 2, and used to determine its nucleotide sequence using the method described in section (2) of Example 3, where a reverse primer for M13 sequencing was used as a sequencing primer. As a result, plasmids lacking 150 bp, 300 bp, 600 bp, 850 bp, 1050 bp, and 1300 bp from the 5' terminal were obtained. The sequences from the 5' terminal of these clones were determined and overlapped to obtain the sequence covering a whole region of cDNA. The obtained sequence agreed completely with the reported sequence of TNF.

EXAMPLE 6

Expression of cDNA in a Mammalian Cell pKATNF1, the sequence of which was determined in Example 5, was introduced into COS7 cells (obtained from ATCC), and the culture supernatant was tested to determine whether it shows TNF activity. The isolated plasmid pKATNF1 was transfected into 5×10$^6$ cells of COS7 using an eletroporation method. After the transfected COS7 cells were cultured in MEM medium for 3 days, the culture supernatant was subjected to a TNF assay using mouse L929 cells (obtained from ATCC). Consequently the supernatant showed a TNF activity of 2.9×10$^3$ units/ml. This means that the SV40 promoter on the vector acts as expected.

TABLE 1

Examples of clone containing in the cDNA bank.

| Clone number | Known Protein showing similarity |
|---|---|
| 1 | HMG14 |
| 2 | HMG17 |
| 3 | Ribosomal protein S14 |
| 4 | Ribosomal protein S17 |
| 5 | Ribosomal phosphoprotein P1 |
| 6 | Elongation factor 1α |
| 7 | Initiation factor 2α |
| 8 | Glyceraldehyde-3-phosphate dehydrogenase |
| 9 | Pyruvate kinase |

TABLE 1-continued

Examples of clone containing in the cDNA bank.

| Clone number | Known Protein showing similarity |
|---|---|
| 10 | β-actin |
| 11 | Profilin |
| 12 | Heat shock protein 90 kDa |
| 13 | Galactosidase A |
| 14 | Laminin binding protein |
| 15 | Plasminogen activator inhibitor 2 |
| 16 | TNF (Tumor Necrosis Factor) |
| 17 | Mitochondria cytochrome b |

We claim:

1. A cloning vector comprising isolated DNA represented by the formula:

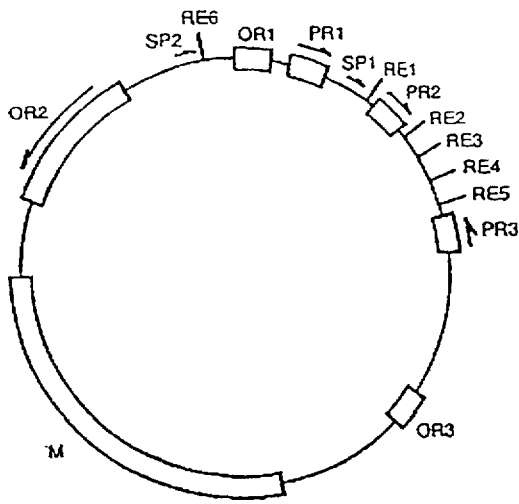

wherein
  PR1 represents a promoter acting in mammalian cells;
  PR2 and PR3 represent promoters for RNA polymerase, which have sequences different from each other;
  SP1 and SP2 represent sequencing primer regions which are different from each other;
  OR1 represents an origin for replication in mammalian cells;
  OR2 represents an origin for replication of a single-stranded phage;
  OR3 represents an origin for replication in E. coli;
  M represents a selectable marker;
  RE1 and RE5 each represent a restriction site selected from the group consisting of Not I, SnaBI, SfiI and SpeI;
  RE2 represents a unique restriction site generating a 3'-protruding dN homooligomer end of about 4 bases after restriction enzyme digestion and wherein RE2 is a recognition site of a restriction enzyme;
  RE3 represents a restriction site;
  RE4 represents a unique restriction site generating a 3'-protruding end after restriction enzyme digestion;
  RE6 represents more than one restriction site generating a 3'-protruding end after restriction enzyme digestion;
  the position of OR2, OR3 and M being arbitrary within the portion of the cloning vector between RE6 and PR3 that is distal from OR1, PR1, SP1, RE1, PR2, RE2, RE3, RE4 and RE5.

2. The cloning vector of claim 1, which is the plasmid pKA1.

3. A vector-primer which is prepared by cutting said cloning vector of claim 1 at the restriction site RE4; adding thereto a dT-tail by terminal deoxynucleotidyl transferase and then cutting the resultant at the restriction site RE3.

4. A vector-primer which is prepared by cutting said vector-primer pKA1 of claim 2 at the restriction site RE4; adding thereto a dT-tail by terminal deoxynucleotidyl transferase and then cutting the resultant at the restriction site RE3.

5. A vector-primer comprising isolated DNA represented by the formula:

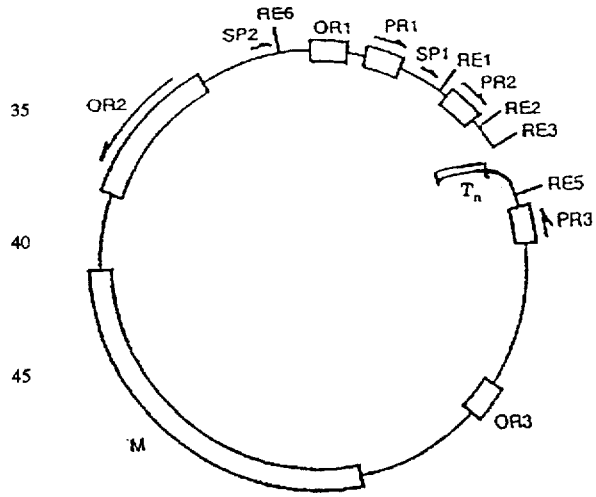

wherein
  PR1 represents a promoter acting in mammalian cells;
  PR2 and PR3 represent promoters for RNA polymerase, which have sequences different from each other;
  SP1 and SP2 represent sequencing primer regions which are different from each other;
  OR1 represents an origin for replication in mammalian cells;
  OR2 represents an origin for replication of a single-stranded phage;
  OR3 represents an origin for replication in E. coli;
  M represents a selectable marker;
  RE1 and RE5 each represent a restriction site selected from the group consisting of Not I, SnaBI, SfiI and SpeI;

RE2 represents a unique restriction site generating a 3'-protruding dN homooligomer end of about 4 bases after restriction enzyme digestion and wherein RE2 is a recognition site of a restriction enzyme;

RE3 represents a restriction site;

$T_n$ represents a poly-dT tail added to the 3' end of the linear vector-primer that is proximal to RE5;

RE6 represents more than one restriction site generating a 3'-protruding end after restriction enzyme digestion;

the position of OR2, OR3 and M being arbitrary within the portion of the cloning vector between RE6 and PR3 that is distal from OR1, PR1, SP1, RE1, PR2, RE2, RE3, RE4 and RE5.

6. The vector-primer of claim 5, which is poly-dT-tailed pKA1.

* * * * *